United States Patent
Zemel

(10) Patent No.: US 8,311,615 B2
(45) Date of Patent: Nov. 13, 2012

(54) SYSTEM AND METHOD FOR VISUALIZING NEEDLE ENTRY INTO A BODY

(75) Inventor: Marc I. Zemel, New Rochelle, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 197 days.

(21) Appl. No.: 12/831,885

(22) Filed: Jul. 7, 2010

(65) Prior Publication Data

US 2011/0009738 A1  Jan. 13, 2011

Related U.S. Application Data

(60) Provisional application No. 61/224,133, filed on Jul. 9, 2009.

(51) Int. Cl.
*A61B 5/05* (2006.01)
*A61B 5/00* (2006.01)
*A61B 6/00* (2006.01)

(52) U.S. Cl. .......... 600/427; 600/310; 600/473

(58) Field of Classification Search .......... 600/310, 600/407, 424, 425, 427, 473, 476
See application file for complete search history.

(56) References Cited

U.S. PATENT DOCUMENTS

| | | | |
|---|---|---|---|
| 5,454,491 A * | 10/1995 | Liu | 222/158 |
| 6,032,070 A | 2/2000 | Flock et al. | |
| 7,280,866 B1 | 10/2007 | McIntosh et al. | |
| 2002/0115922 A1 | 8/2002 | Waner et al. | |
| 2008/0194930 A1 * | 8/2008 | Harris et al. | 600/310 |

FOREIGN PATENT DOCUMENTS

| WO | WO 01/52835 A2 | 7/2001 |
|---|---|---|
| WO | WO 2006/073869 A2 | 7/2006 |
| WO | WO 2009/021064 A1 | 2/2009 |

OTHER PUBLICATIONS

Subhadra Srinivasan, "Interpreting Hemoglobin and Water Concentration, Oxygen Saturation, and Scattering Measured in vivo by Near-Infrared Breast Tomography," PNAS, vol. 100, No. 21, pp. 12349-12354, Oct. 14, 2003.

* cited by examiner

*Primary Examiner* — Michael Rozanski

(74) *Attorney, Agent, or Firm* — Mony R. Ghose; Craig Metcalf; Kirton McConkie

(57) ABSTRACT

A system for visualizing needle entry into a body is presented. The system includes a needle for entering a body. The needle is coated with a radiation scattering coating on at least a portion of the needle. The system additionally includes a radiation visualization device which detects reflected radiation directed at a target body and enables medical personnel to view anatomical structures such as a blood vessel along with the inserted needle within a body.

14 Claims, 4 Drawing Sheets

SYSTEM AND METHOD FOR VISUALIZING NEEDLE ENTRY INTO A BODY

RELATED APPLICATIONS

This application claims the benefit of U.S. Provisional Application No. 61/224,133, filed Jul. 9, 2009, entitled NEEDLE COATING FOR ENHANCED VISUALIZATION. This application claims priority to and incorporates herein by reference the provisional application.

BACKGROUND OF THE INVENTION

The present invention relates to a system and method for visualizing a needle within biological tissue. More particularly, the invention relates to a system and method for visualizing a needle and locating anatomical structures within a body by utilizing equipment sensitive to the unique absorption and scattering characteristics of the target structures.

Every day many hundreds-of-thousands of medical procedures involving the puncturing of blood vessels are performed. Venipuncture, as it is known, is required in order to administer emergency fluids, blood components, and anesthetics during operations, or to allow the drawing of blood for biochemical analysis. Venipuncture, which is often the rate-limiting step when administering intravenous compounds, can take as long as a half hour, or longer when the patient is a neonate, infant, geriatric, obese, or burn patient. Notwithstanding the enormous financial burden on our society as a whole because operating rooms and health-care providers must wait as an intravenous line is placed, the delay in placing an intravenous line can in fact be life threatening. Furthermore, there are additional problems associated with multiple venipunctures caused by the clinician's failure to locate the vessel.

The reason venipuncture is sometimes difficult to do is that the blood vessels are often located relatively deep within the tissue which, because of its absorptive and scattering optical properties, makes visualization of the blood vessel impossible under normal conditions. Furthermore, the situation is made worse by the fact that the vessel may spasm and constrict if it is manipulated too much. Consequently, health care providers have a need to visualize blood vessels in real-time during venipuncture in order to reduce the risk to the patient, save time and reduce the cost of the procedure. Furthermore, reducing the time of the procedure limits the providers' exposure to a potentially contaminated needle. Finally, visualization of vascular tissue can provide important diagnostic and therapeutic information about certain diseases such as thromboses, cancers or vascular malformations.

In the mid-1970's an instrument was devised that purportedly provided surgeons with the ability of visualizing superficial blood vessels. It consisted of a visible light source which, when pressed up against the skin, transilluminated the subcutaneous tissue and aided in the visualization of superficial blood vessels. The blood-vessel transilluminator made use of the different absorption properties of blood and tissue. Because blood strongly absorbs certain wavelengths of light, while fat and skin absorb other wavelengths, a health-care provider purportedly could visually distinguish the position of the subcutaneous blood vessel with the naked eye. The transilluminator has essentially fallen into disuse because it fails to provide enough contrast between the blood vessel and tissue to be of use other than for venipuncture of superficial vessels. Furthermore, some versions of the blood-vessel transilluminator caused thermal damage to the patient.

In response to the transilluminator's failures, several references proposed using an illumination wavelength which penetrates surface tissue to a depth of the deep vessels but which is also highly absorbed by the blood. See, e.g., Cheong, W-F, et al., "A Review of the Optical Properties of Biological Tissues," IEEE Journ. Quant. Elec., 26:2166-2185 (1990). These references, however, did not disclose efficient means of effectively illuminating and detecting the body structures of a vessel.

Later devices produced more effective results by employing a polarizer to detect back-scattered illumination reflected from a body. See e.g. U.S. Pat. No. 6,032,070, entitled Method and Apparatus for Detecting Electro-magnetic Reflection from Biological Tissue, which is herein incorporated by reference. Using reflected electromagnetic radiation singularly scattered from target tissue, these methods enabled medical personnel to effectively view anatomical structures such as blood vessels in high contrast with its surrounding tissue. Accordingly, present procedures enable medical clinicians to visualize internal anatomical structures such as blood vessels.

BRIEF SUMMARY OF THE INVENTION

The systems and methods of the present disclosure have been developed in response to problems and needs in the art that have not yet been fully resolved by currently available techniques. Thus, these systems and methods are developed to enable medical personnel to visualize not only internal anatomical structures, but also a needle within a body.

In one aspect, a system is provided for visualizing needle entry into a body that includes a needle, a radiation scattering coating (herein occasionally referred to simply as a "coating" or a "needle coating"), and a radiation visualization device. The radiation scattering coating may be a near infrared radiation scattering coating or an infrared radiation scattering coating. The needle coating is coated on at least a portion of the needle.

Some implementations may include one or more of the following features. The coating may include one or more polymers. The coating may include fluorinated ethylene propylene (FEP) or polytetrafluoroethylene (PTFE). The coating may include at least one of a pigment and a dye that scatters incident near infrared radiation. The coating may include a saturating feature, such as a channel, a groove, or a pore. The coating may be coated only on the needle tip. Alternatively, the coating may be coated the entire needle except the needle tip. The coating may coat the needle using a pattern of coated and uncoated portions. The radiation visualization device may include a detector that visualizes based on tomography, spectroscopy, or spectral imaging.

In another aspect, a system for visualizing needle entry into a body includes a needle, a radiation scattering coating coated on the needle, the coating including at least one of fluorinated ethylene propylene (FEP) and polytetrafluoroethylene (PTFE), the coating further including at least one of a radiation scattering pigment and a radiation scattering dye, and a radiation visualization device.

Some implementations may include one or more of the following features. The coating may include a saturating feature. The coating may be coated only on the needle tip of the needle. The radiation visualization device may include a detector that visualizes based on tomography, spectroscopy, or spectral imaging.

In another aspect, a method of visualizing needle entry into a blood vessel includes providing a needle having a radiation scattering coating, providing a radiation visualization device, inserting the needle into a body, and monitoring the advancement of the needle toward a blood vessel using the radiation visualization device.

Some implementations may include one or more of the following features. Needle advancement may be stopped when the needle tip is visualized as entering a blood vessel of the body. A saturating feature may be included on the needle coating. The radiation scattering coating may be disposed only on the needle tip of the needle.

Thus, implementations of the present systems enable a medical clinician to visualize not only internal anatomical structures, but also a needle as it is advanced into a body. As clinicians are enabled to visualize internal structures, venipuncture procedures may be performed more rapidly and accurately.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

Embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
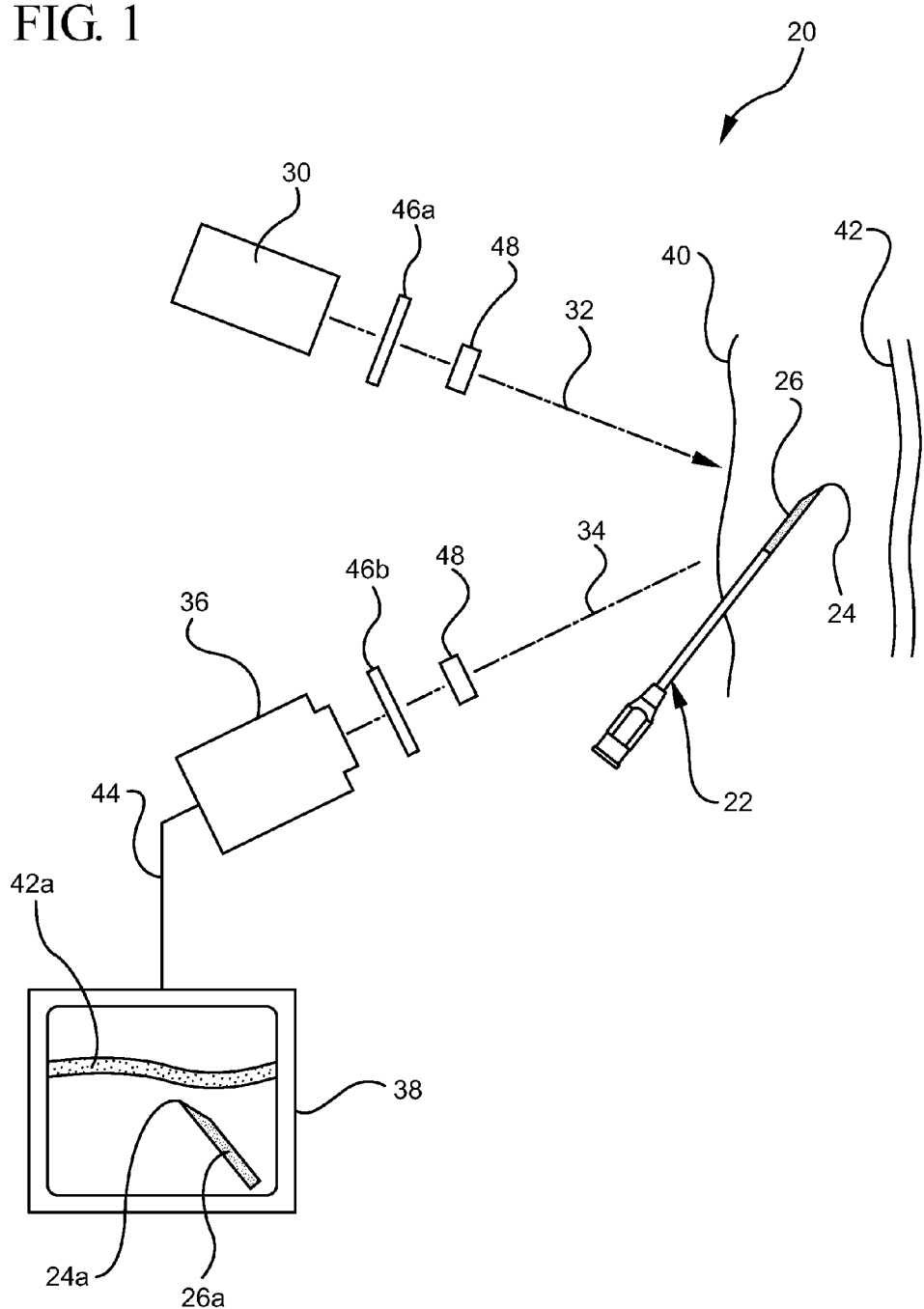
FIG. 1 is a schematic diagram of an imaging system and a needle with a radiation scattering coating in accordance with a representative embodiment.

FIG. 1 illustrates an embodiment of a system for visualizing needle entry into a body. The system includes a radiation visualization device or system 20 (e.g. Digital VeinVue from VueTek Scientific) which includes a radiation light source 30, a radiation detector 36, and a display 38. In some embodiments the radiation is infrared (IR) radiation, in other embodiments the radiation is near infrared radiation (NIR). To view interior anatomical structures, the light source 30 radiates a beam of incident light 32 upon a biological tissue 40, such that the beam is partially transmitted through the biological tissue until being absorbed by the target anatomical structure 42. An image detector 36, (e.g. Model CCD-72 camera available from Dage-MTI, Inc.) detects reflected light 34, predominantly reflected from tissue surrounding the target anatomical structure with a different absorptive wavelength than the anatomical structure. The image detector 36 is connected by a video signal 44 to the monitor 38 so that the intensity information of incident light reflected from the tissue is displayed onto the monitor in the form of an image.

During or after imaging is initiated, a needle 22 may be inserted into the biological tissue 40 and be directed towards the target anatomical structure 42. As the needle advances, light 32 from the light source 30 radiates upon the needle 22 and is scattered by the radiation scattering coating 26 (herein occasionally referred to simply as a "coating" or a "needle coating") that is coated on the needle 22. Simultaneously, light 32 incident upon the uncoated portions of the needle 22 is absorbed in a greater degree than that incident upon the coating 26. Accordingly, more light 34 is reflected from the coated portions 26 of the needle 22 than from the uncoated portions. The reflected light 34 is detected by the detector 36 and imaged by the monitor 38. The monitor will thus image the shape of the target anatomical structure 42 and the coated portion of the needle 22. In this manner, the medical personnel can direct the needle tip 24 into the target anatomical structure 42. Accordingly, in some embodiments, the needle coating 26 is a radiation scattering coating. Alternatively, in other embodiments, the needle coating 26 is a radiation absorbing coating, wherein the needle coating is distinguished from the more opaque background or target anatomical structure.

A radiation scattering coating can assist medical personnel during various medical procedures. Accordingly, the radiation scattering coating can be applied to various needle types. For instance, in some embodiments the needle is a hypodermic needle. In other instances the needle is an introducer needle used in over the needle catheter placement procedures. Alternatively or additionally, the radiation scattering coating is applied to a catheter, used with an introducer needle. In other embodiments, the radiation scattering coating is coated onto a rigid catheter. Herein the term "needle" will include standard needles, such as hypodermic needles, as wells as catheters and other like devices that may be used to access an anatomical structure near the outer surface of a body and/or deliver a fluid thereto.

Various coatings reflect or absorb radiation to produce the desired effect when coated on a needle 22 and used with an radiation visualization device. Accordingly, various coating types can be applied to the needle. In some embodiments the coating is a polymer or copolymer. For example, in one embodiment the coating includes fluorinated ethylene propylene (FEP) that is applied to the needle view melt extrusion, coating, or impregnation (e.g. Neoflon® from Daikin, and Hostaflon® from Hoechst). In some embodiments, the coating includes polytetrafluoroethylene (PTFE) (e.g. Teflon®FEP from Dupont). Since FEP has may be highly transparent it can be coated onto a needle without being noticeable or distracting to patients or medical personnel.

Additionally or alternatively, in some embodiments, the needle 22 or the needle coating 26 includes a pigment or a dye that scatters incident near infrared radiation. For example, indocyanine-green (ICG) dye absorbs strongly near 800 nm, where tissue is relatively transmitting. (Flock, S. et al., "Thermal Damage of Blood Vessels using Insocyanine Green and a Pulsed Alexandrite Laser," Lasers Med. Sci., 8:185-196 (1993)). Accordingly, an ICG dye disposed with a needle coating or coated on a needle may reflect 800 nm illumination. In other embodiments, other NIR/IR-opaque or NIR/IR-reflective substances are applied to the needle 22 or needle coating 26.

Figure 4:
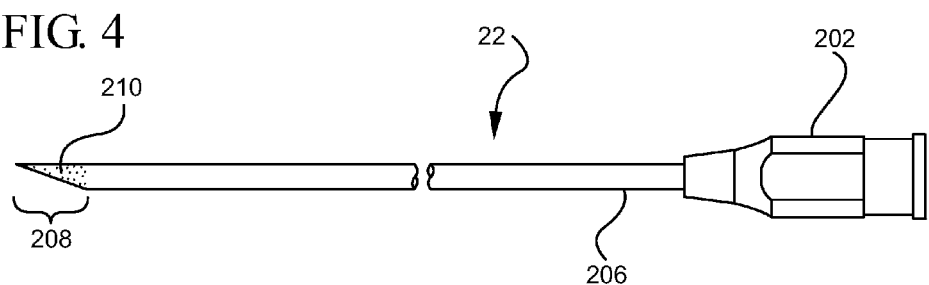
FIG. 4 is a perspective view of a needle having a radiation scattering coating in accordance with a representative embodiment.
Figure 5:
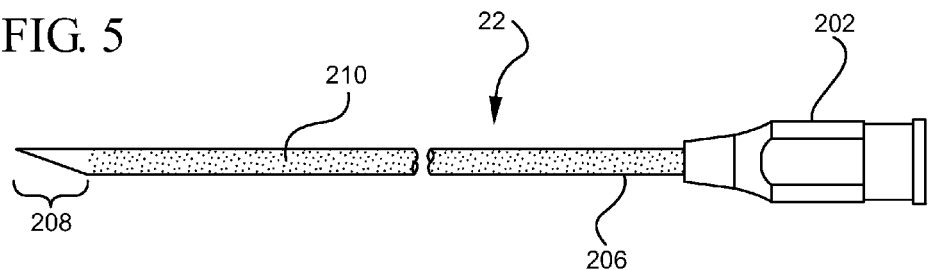
FIG. 5 is a perspective view of a needle having a radiation scattering coating in accordance with another representative embodiment.
Figure 6:
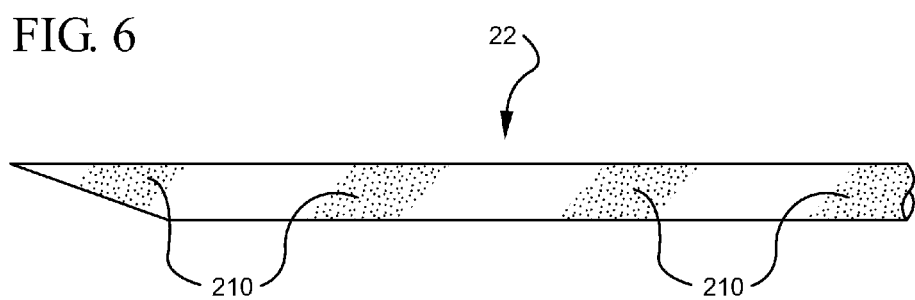
FIG. 6 is a perspective view of a needle having a radiation scattering coating in accordance with yet another representative embodiment.

To enhance visualization of the displayed image, the needle coating 26 can be applied to the entire needle 22, the needle tip 24 (shown in FIGS. 1-2 and 4), or the entire needle minus the needle tip (shown in FIG. 5). Additionally, in some embodiments, a pattern of needle coating 26 is applied to the needle 22 as alternating coated and uncoated regions, as shown in FIG. 6.

NIR radiation enables medical personnel to detect signal reflection through as much as twelve centimeters of body tissue. ("Interpreting Hemoglobin and Water Concentration, Oxygen Saturation, and Scattering Measured in Vivo by Near-infrared Breast Tomography," Sudhadra Sinivasan et. al. PNAS, Oct. 14, 2003, vol. 100, no. 21). Additionally, very high contrast images can be produced at depths up to 1.5 centimeters. NIR illumination is particularly useful for imaging blood vessels or veins.

During imaging procedures, the location of the vessel or vein in relation to the needle tip 24 is critical to proper needle placement. Absent a needle coating, the needle directs the majority of incident light away from the detector 36. This effect makes it difficult to determine when the needle has entered the vein because the vein also appears black in the display 38. Accordingly, the needle tip may be coated or uncoated so as to provide a distinct image of the needle tip during imaging, based on the nature of the coating.

As illustrated, in some instances, the display 38 depicts the blood vessel 42a as darker than the surrounding tissue. In this manner a clinician visualizes the location of the blood vessel 42a. Further, in some embodiments, the properties of the needle coating cause the coating to be displayed as darker in the display. Thus, the clinician can direct a darker, coated needle tip into the blood vessel accurately and quickly. In other embodiments, the properties of the needle coating lead it to be displayed as a lighter object, and in this situation a coated tip will be displayed as the lighter object that can disappear into the darker blood vessel in ensure proper needle tip 24 placement. Accordingly, the needle coating enables medical personnel to more effectively introduce a needle into a body.

The needle 22 and needle coating 26 can be utilized with a variety of radiation visualization systems. The radiation visualization system 20 of FIG. 1 illustrates just one of several possible embodiments of a radiation visualization systems or devices that may be utilized with the present needle and needle coatings. For the purpose of illustration, the operation and configuration of the visualization system 20 will now be explained. First, to view interior anatomical structures the light source 30 radiates a beam of incident light 32 upon a biological tissue 40, such that the beam is partially transmitted through the biological tissue until being absorbed by the target anatomical structure 42. An image detector 36, (e.g. Model CCD-72 camera available from Dage-MTI, Inc.) detects reflected light 34, predominantly reflected from tissue surrounding the target anatomical structure with a different absorptive wavelength than the anatomical structure.

In some embodiments, the image detector 36 is connected by a video signal 44 to the monitor 38 so that the intensity information of incident light reflected from the tissue is displayed onto the monitor in the form of an image. If a polychromatic light source is used, wavelengths outside the useful range for imaging the target structure should be filtered out by one or more bandpass filters 48. Alternatively, the imaging detector can detect only wavelengths within the useful range, such as occurs with a charge-coupled device infrared camera (CCD) (e.g. CCD1350-1 infrared CCD camera and 9300-00 image intensifier available from Electrophysics Corp. Fairfield N.J.). Alternatively, a real-time digital image processor (e.g. CSP-2000 Processor available from Dage-MTI Inc.) can be used to filter out information poor wavelengths generated by the polychromatic light source.

In an alternative embodiment of the invention, a polarizing optical element 46a such as a polarizing filter (e.g. available from Ealing Electro-Optics Ind., Holliston, Mass. or Oriel Corp., Stratford, Conn.) is used in combination with a laser or other monochromatic light source. Monochromatic sources include, by way of example, the Model 6124 laser diode available from New Focus, Inc. Sunnyvale Calif., the Model Micralase available from Micracor, Inc., Acton Mass., and the MDL-DLAW10 available from McDonnell Douglas Aerospace, St. Louis Mo. The polarizing filter, by polarizing the incident light in a particular plane with respect to the tissue will cause the singularly reflected light to be of a distinct polarization. A second polarizing optical element 46b in front of the detector then preferentially selects out singularly reflected radiation from the light source. Multiply scattered radiation, which carries little image information, is typically randomly polarized and thus will not pass through the second polarizing optical element 46b and onto the image detector 12. The polarizing filters can be used with either the bandpass filter 48, the charge-coupled device infrared camera or any combination of these in the event a polychromatic light source is used for the light source 30. Any combination of these elements may also be used when the light source 30 comprises a laser or other monochromatic light source.

In other embodiments, the system incorporates other imaging systems for imaging the internal anatomical structures of a body. For example, in some embodiments, the imaging system utilizes a digital image processor, a frame grabber (such as the CSP-2000 processor available from Dage-MTI Inc.), and a light source that projects at least two wavelengths. In some embodiments, the imaging system utilizes collimators to eliminate scattered light.

In some embodiments, the imaging system performs phase-modulated detection of the reflected image 34. In these embodiments, incident laser light 34 is phase modulated by a modulation source 30 which controls a light phase modulator 28 such as a rotating aspheric optic or a Kerr cell (e.g. available from Meadowlark Optics, Longmont Colo., Advanced Optronics Inc., San Jose Calif., or Ninds Instruments Inc., Nillsboro Oreg.) The modulation source controls the phase-sensitive imaging detector such as a liquid crystal video television. Thus, the image detector only measures the reflected light that has the same state of modulation as the incident light. All other light is removed from the measurement.

Figure 2:
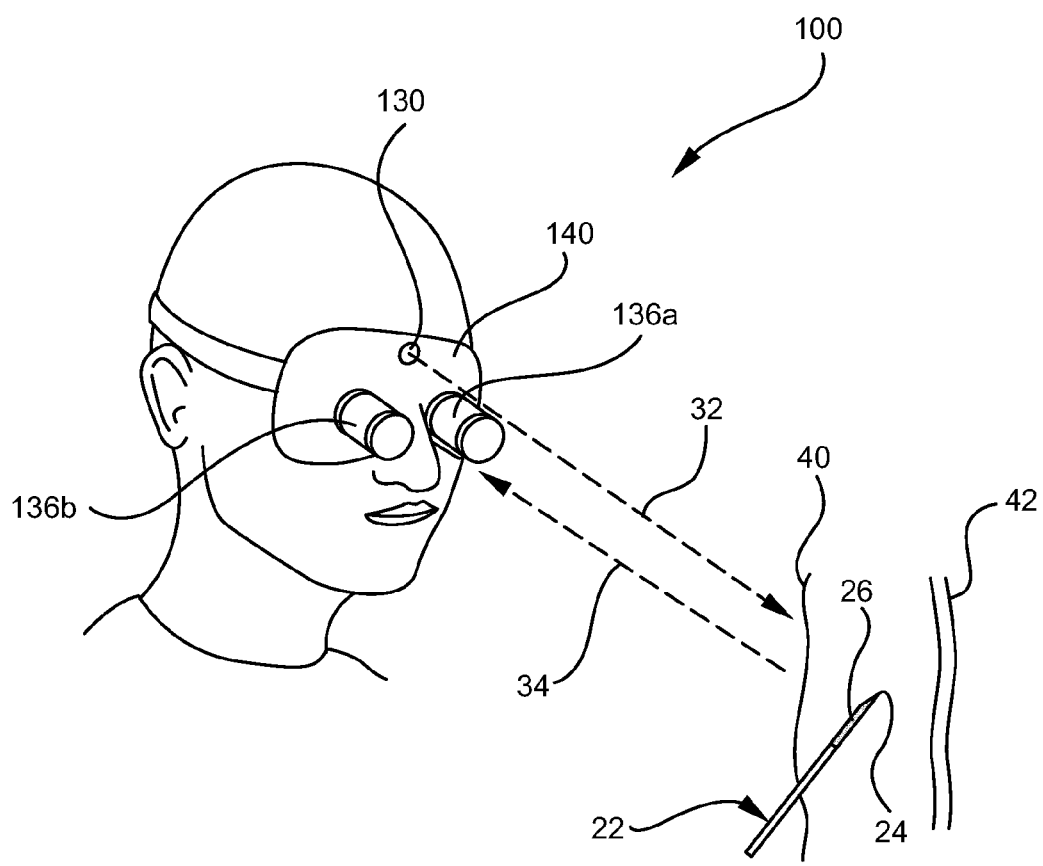
FIG. 2 is a schematic diagram of an imaging system incorporated into a helmet apparatus and a needle with a needle coating in accordance with a representative embodiment.

Referring now to FIG. 2, in some embodiments, the imaging system 100 utilizes binocular stereo imaging of a target anatomical structure. In these embodiments, three dimensional depth information is incorporated within the image by detecting two angles of reflected light from the target tissue area using two imaging detectors 136a and 136b (e.g. Model 8900 infrared sensitive video cameras with focusing eyepieces and objective lenses from FJW Optical Systems Inc., Palatine, Ill.) In one variation of this embodiment a light source 130 (e.g. MDL-DLAW10 diode laser from McDonnell Douglas Aerospace, St. Louis, Mo., with LD1001 driver from Thor-Labs, Newton N.J. and 12 V DC source) is mounted on a helmet (e.g. The Physician's Headlight from Welch-Allyn Inc., Skaeneateles Falls, N.Y.) which in turn holds the two imaging detectors 136a and 136b. The light source output may optionally be focused with diode laser collimation optics (e.g. Model LT110P-B from Thor-Labs, Newton, N.J.) to produce about a 1 mm spot at a distance of about 20 inches. The incident light 32 is reflected back from the target tissue as 34. Variations of the binocular stereo imaging system may be incorporated into the present systems and methods.

Figure 3:
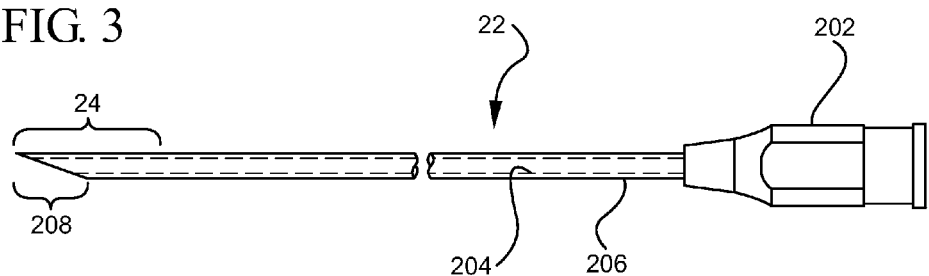
FIG. 3 is a perspective view of a needle in accordance with a representative embodiment.

Referring now to FIG. 3, a needle 22 is depicted according to a representative embodiment. The needle includes a needle hub 202 disposed at the proximal end of the needle 22. A needle shaft 206 extends from the distal end of the needle hub 202. A beveled needle tip 208 is formed in the distal end of the needle to facilitate entry into a body. The needle also includes a distal portion 24 which is approximately two to three times the distance of the needle tip.

In some embodiments, the needle coating 210 is coated only on the needle tip 208, as shown in FIG. 4, or only on the distal portion 24 of the needle. Alternatively, in some embodiments, the needle coating 210 is coated on the entire needle shaft 206 minus the needle tip 208, as shown in FIG. 5. In other embodiments, the needle coating 210 is coated either on the shaft 206, the needle tip 208, or the distal end 24 using a pattern of coated and uncoated portions, as shown in FIG. 6. The needle further includes an interior lumen 204 that extends through the needle from the distal to the proximal end.

Figure 7:
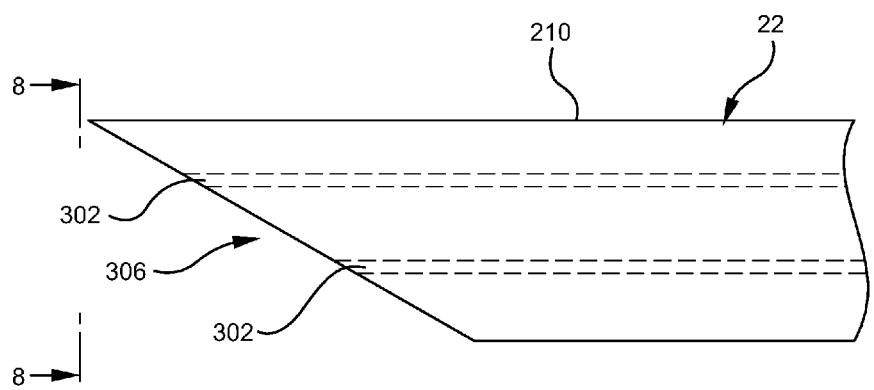
FIG. 7 is a perspective view of a needle tip having a radiation scattering coating with a saturating feature in accordance with yet another representative embodiment.

Referring now to FIG. 7, a needle 22 is depicted as having a needle coating 210. One or more saturating features 302 may be included within the needle coating 210. A saturating feature enables blood to fill up, wick, or otherwise saturate the needle coating 210 in order to defeat the scattering properties of the coating. In some embodiments, blood absorbs or scatters radiation differently than the needle coating 210, accordingly, when blood saturates the coating, which may be transparent, radiation incident on the saturated coating responds the same or substantially the same as a blood vessel. Thus, when medical personnel view the image of the reflected light 34 on the display 38, the saturation of the needle coating 210 can be watched to ensure that the blood vessel is properly accessed.

When used with needles having a flashback feature, the saturation feature 302 enables medical personnel to visualize flashback along the needle before it is directly visible without a radiation visualization device. For example, when using the radiation visualization device along with a needle 22 having a needle coating 210 medical personnel can visualize entry of the needle tip into a target anatomical structure, such as a blood vessel. As blood begins to flow along the needle, such as between an introducer needle and a catheter, the medical personnel, still using the radiation visualization device, can see the flashback as the blood defeats the needle coating 210. Since blood may be displayed as darker than the coating, as it saturates the saturation feature(s) 302 by making the coating appear darker. Such features enable medical personnel to conduct the entire needle insertion process using the radiation visualization device/system rather than watching both the display and the needle insertion site.

Figure 8A:
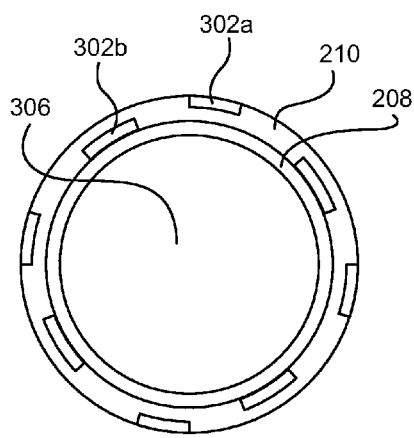
FIG. 8A is a front view of a needle tip having a radiation scattering coating with a saturating feature, taken along Line 8-8 of FIG. 7, in accordance with yet another representative embodiment.
Figure 8B:
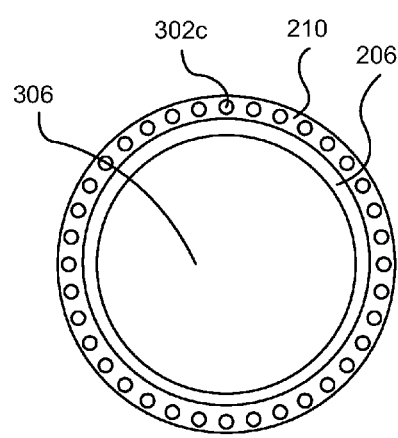
FIG. 8B is another front view of a needle tip having a radiation scattering coating with a saturating feature in accordance with yet another representative embodiment.

In some embodiments the saturation feature is one or more of a channel, pore, groove, or other like feature within the needle coating. Referring now to FIGS. 7-8B, in some embodiments the needle coating includes one or more saturation features that extend down the length of the needle 22. FIGS. 8A and 8B illustrate front views of a distal end of a needle taken along line 8 of FIG. 7. As depicted, the needle shaft 206 includes an internal lumen 306 and an external needle coating 210. The coating includes one or more saturation features 302a and 302b in the form of channels or grooves that extend at least partially into the needle coating and along the length of the needle. In some embodiments, the saturation features 302a are disposed on the exterior of the needle coating. In other embodiments the saturation features 302b are disposed on the interior of the needle coating. Additionally, in some embodiments, the saturation features 302c are disposed throughout the needle coating, as shown FIG. 8B. Blood may flow along or through the saturation features 302a-302c or be wicked therein.

Figure 9:
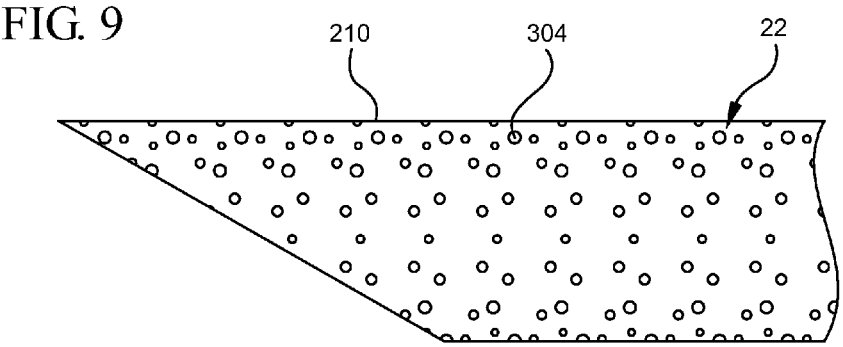
FIG. 9 is a perspective view of a needle tip having a radiation scattering coating with a saturating feature in accordance with yet another representative embodiment.

FIG. 9 depicts a needle coating 210 on a needle 22. The needle coating 210 includes a plurality of pores 304 which function as saturation features. As blood comes in contact with the needle coating it is drawn therein via wicking or other means. Once within the needle coating, the blood defeats the needle coating and enables a medical practitioner to recognize that blood has been saturated within the needle coating. Accordingly, the saturation features enable flashback to be recognized along the needle that is disposed within a body, prior to the flashback being visible exterior to the body.

Thus, embodiments of the present systems enable a medical clinician to visualize not only internal anatomical structures, but also a needle as it is advanced into a body. The application of a radiation scattering coating on a needle enables clinicians to visualize internal structures of a body. The enhanced visualization may enable venipuncture procedures to be performed more rapidly and accurately that possible in the absence of a needle with a radiation scattering coating.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A system for visualizing needle entry into a body, comprising:
   a needle;
   a radiation scattering coating coated on the needle, the radiation scattering coating having a saturating feature comprising a pore; and
   a radiation visualization device.

2. The device of claim 1, wherein the coating includes at least one polymer.

3. The device of claim 1, wherein the coating includes at least one of fluorinated ethylene propylene (FEP), polytetrafluoroethylene (PTFE), and combinations thereof.

4. The device of claim 1, wherein the coating includes at least one of a pigment and a dye that scatters incident near infrared radiation.

5. The device of claim 1, wherein the coating is coated only on the needle tip of the needle.

6. The device of claim 1, wherein the coating is coated on the needle except the needle tip.

7. The device of claim 1, wherein the coating is coated on the needle using a pattern of coated and uncoated portions.

8. The device of claim 1, wherein the radiation visualization device includes a detector that visualizes based on at least one of tomography, spectroscopy, and spectral imaging.

9. A system for visualizing needle entry into a body, comprising:
    a needle; and
    a radiation scattering coating coated on the needle, the coating further including a radiation scattering pigment or a radiation scattering dye having a saturating feature comprising a pore.

10. A device of claim 9, wherein the coating includes at least one of fluorinated ethylene propylene (FEP), polytetrafluoroethylene (PTFE), and combinations thereof.

11. A device of claim 10, wherein the coating is coated on the needle using a pattern of coated and uncoated portions.

12. A method visualizing needle entry into a blood vessel, comprising:
    providing a needle having a radiation scattering coating comprising a saturating feature that is a pore;
    providing a radiation visualization device;
    inserting the needle into a blood vessel;
    blocking the radiation scattering coating by saturating the pore of the saturating feature with blood; and
    visualizing advancement of the needle into a blood vessel by monitoring the saturation of the pore of the saturating feature with the radiation visualization device.

13. The method of claim 12, further comprising a step for stopping advancement of the needle into the blood vessel when the needle tip of the needle is visualized as within the blood vessel.

14. The method of claim 12, further comprising a step for coating a tip portion of the needle with the radiation scattering coating.

* * * * *